US008415519B2

(12) United States Patent
Vaughn et al.

(10) Patent No.: US 8,415,519 B2
(45) Date of Patent: Apr. 9, 2013

(54) METHODS FOR DETERMINING EFFICACY OF METAL OXIDE CO-CATALYSTS FOR OXYGENATES-TO-OLEFINS REACTIONS

(75) Inventors: Stephen N. Vaughn, Kingwood, TX (US); Sebastien P. B. Kremer, Woluwe-Saint-Lambert (BE); Teng Xu, Hampton, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 786 days.

(21) Appl. No.: 12/337,378

(22) Filed: Dec. 17, 2008

(65) Prior Publication Data

US 2010/0152514 A1 Jun. 17, 2010

(51) Int. Cl.
*C07C 1/20* (2006.01)

(52) U.S. Cl. ........ 585/640; 585/638; 585/639; 585/502; 502/65; 502/208; 502/214; 502/240; 502/263

(58) Field of Classification Search .................. 585/638, 585/639, 640; 502/208, 214, 240, 263, 65; 260/668 R, 682

See application file for complete search history.

(56) References Cited

U.S. PATENT DOCUMENTS

| | | | | |
|---|---|---|---|---|
| 4,062,905 | A * | 12/1977 | Chang et al. | 585/640 |
| 6,844,291 | B2 | 1/2005 | Levin et al. | |
| 6,906,232 | B2 | 6/2005 | Levin et al. | |
| 6,995,111 | B2 | 2/2006 | Levin et al. | |
| 7,166,757 | B2 | 1/2007 | Fung et al. | |
| 7,186,875 | B2 | 3/2007 | Fung et al. | |
| 7,199,277 | B2 | 4/2007 | Xu et al. | |
| 7,199,278 | B2 | 4/2007 | Fung et al. | |
| 7,208,442 | B2 | 4/2007 | Xu et al. | |
| 2005/0137439 | A1 | 6/2005 | Smith | |
| 2008/0103345 | A1 | 5/2008 | Levin et al. | |

OTHER PUBLICATIONS

Lavalley, J.C.; "Infrared Spectrometric Studies of the Surface Basicity of Metal Oxides and Zeolites Using Adsorbed Probe Molecules," Catalysis Today, vol. 27, pp. 377-401, 1996.

Lima, Enrique, et al.; "Characterization of the Acid-Base Properties of Oxide Surfaces by C CP/MAS NMR Using Adsorption of Nitromethane," J. Phys. Chem., vol. 107, pp. 4070-4073, 2003.

Kheir, Ali A., et al.; "Chemisorption of Aci-Nitromethane on Strongly Basic Catalysts: An NMR Probe of Solid Basicity," J. Am. Chem. Soc., vol. 116, pp. 817-818, 1994.

* cited by examiner

*Primary Examiner* — In Suk Bullock
*Assistant Examiner* — Candace R Chouinard
(74) *Attorney, Agent, or Firm* — Kevin M. Faulkner; Gerard J. Hughes

(57) ABSTRACT

The invention involves a process for converting an oxygenate-containing feed into an olefin-containing product comprising: (a) providing a co-catalyst oxide of a metal from Groups 2-4 of the Periodic Table of Elements, Lanthanides, Actinides, and combinations thereof, (b) contacting the metal oxide with nitromethane under conditions sufficient for the nitromethane to adsorb onto the metal oxide; (c) analyzing the nitromethane-adsorbed metal oxide using NMR to determine a basic site density of the metal oxide; (d) providing a catalyst system comprising a primary catalyst comprising aluminosilicates, aluminophosphates, silicoaluminophosphates, and metal-containing derivatives and combinations thereof, and the co-catalyst metal oxide whose basic site density is ≧0.085 mmol/g and whose BET surface area is ≧20 $m^2/g$; (e) contacting the oxygenate-containing feedstock with the catalyst system under conditions sufficient to form an olefin-containing product; and (f) separating the olefin-containing product into at least ethylene and/or propylene.

8 Claims, 1 Drawing Sheet

METHODS FOR DETERMINING EFFICACY OF METAL OXIDE CO-CATALYSTS FOR OXYGENATES-TO-OLEFINS REACTIONS

FIELD OF THE INVENTION

This invention provides a method of selecting preparation conditions for metal oxide co-catalysts for use in oxygenates-to-olefins (OTO) reactors.

BACKGROUND OF THE INVENTION

The use of metal oxides (MOs) in methanol-to-olefins (MTO) reactions has been described in detail in several publications, including U.S. Pat. Nos. 6,844,291, 6,906,232, 6,995,111, 7,166,757, 7,186,875, 7,199,277, 7,199,278, and 7,208,442, as well as U.S. Patent Application Publication Nos. 2005/0137439 and 2008/0103345.

One problematic aspect of MO use is the fact that not every example of a given chemical formulation is effective in generating the benefits ascribed to their use. For example, some samples of yttria MO ($Y_2O_3$) are virtually inactive as co-catalysts, while other examples may be effective.

We have previously disclosed that $CO_2$ adsorption at 100° C. may be used to differentiate the various examples of MOs (U.S. Pat. No. 6,844,291). However, there is a possibility that $CO_2$ can react stoichiometrically with the MO to form the respective carbonates, even in the absence of basic sites on the MO to, in effect, give a false reading of the potential activity of the MO as a lifetime extension co-catalyst in OTO (MTO) use.

A more specific and targeted probe of the basic sites would be useful in selecting both potential MOs and in directing the preparation steps to avoid inadvertently deactivating the MO prior to or during use. Therefore, there is a need to provide a method of selecting and monitoring the quality of the MO for use as a co-catalyst in OTO (MTO) reactions.

SUMMARY OF THE INVENTION

One aspect of the invention relates to a method for determining basic site density in a metal oxide co-catalyst for use in an oxygenate-to-olefins conversion reaction, the method comprising: (a) providing an oxide of at least one metal selected from the group consisting of Groups 2, 3, and 4 of the Periodic Table of Elements, Lanthanides, Actinides, and combinations thereof, (b) contacting the metal oxide with nitromethane under conditions sufficient for the nitromethane to adsorb onto the metal oxide; (c) analyzing the nitromethane-adsorbed metal oxide using NMR to determine a basic site density of the metal oxide; and (d) determining if the basic site density is sufficient to indicate that the metal oxide would be useful as a co-catalyst in an oxygenate-to-olefins conversion reaction.

Another aspect of the invention relates to a process for converting an oxygenate-containing feed into an olefin-containing product, the process comprising: (a) providing, as a co-catalyst, an oxide of at least one metal selected from the group consisting of Groups 2, 3, and 4 of the Periodic Table of Elements, Lanthanides, Actinides, and combinations thereof; (b) contacting the metal oxide with nitromethane under conditions sufficient for the nitromethane to adsorb onto the metal oxide; (c) analyzing the nitromethane-adsorbed metal oxide using NMR to determine a basic site density of the metal oxide; (d) providing a catalyst system comprising a primary catalyst selected from the group consisting of aluminosilicates, aluminophosphates, silicoaluminophosphates, metal-containing derivatives thereof, and combinations thereof, and the metal oxide as a co-catalyst, wherein the basic site density of the metal oxide is at least 0.085 mmol/g, and wherein the metal oxide has a BET surface area of at least 20 $m^2/g$; (e) contacting the oxygenate-containing feedstock with the catalyst system under conditions sufficient to form an olefin-containing product; and (f) separating the olefin-containing product into at least ethylene and/or propylene.

Advantageously, a process for forming an olefin-containing polymer and/or oligomer according to the invention can include: (a) converting an oxygenate-containing feed into an olefin-containing product according to the process of the previous paragraph; and (b) oligomerizing and/or polymerizing the ethylene and/or propylene separated from the olefin-containing product, optionally in conjunction with one or more olefin-forming catalysts, and optionally along with one or more additional comonomers, under conditions sufficient to form the olefin-containing polymer and/or oligomer.

DETAILED DESCRIPTION OF THE EMBODIMENTS

Figure 1:
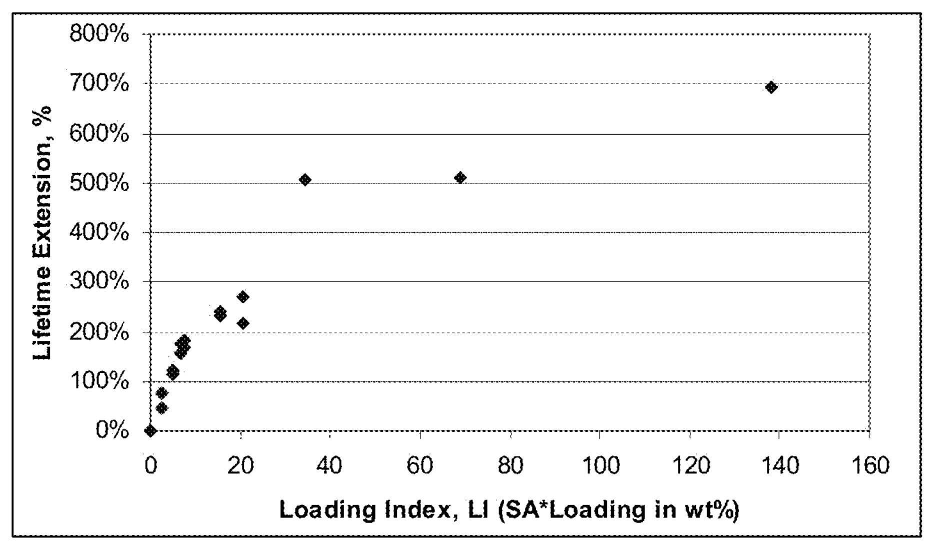
FIG. 1 illustrates the impact of loading index (LI) on lifetime extension index (LEI) for a SAPO-yttria catalyst system.

It has been found that combining a primary molecular sieve catalyst with one or more active MOs results in a catalyst system composition with an enhanced olefin yield and/or a longer catalyst system lifetime, when used in the conversion of oxygenate-containing feedstocks, particularly methanol-containing feedstocks, into one or more olefins, particularly prime olefins such as ethylene and/or propylene. In addition, the resultant catalyst system composition can tend to be more propylene selective and can tend to yield lower amounts of unwanted ethane and propane, together with other undesirable compounds, such as aldehydes and ketones, specifically acetaldehyde.

Molecular sieves have been classified by the Structure Commission of the International Zeolite Association according to the rules of the IUPAC Commission on Zeolite Nomenclature. According to this classification, framework-type zeolite and zeolite-type molecular sieves, for which a structure has been established, are assigned a three letter code and are described in the *Atlas of Zeolite Framework Types,* 5th edition, Elsevier, London, England (2001), which is herein fully incorporated by reference.

Crystalline molecular sieves all have a 3-dimensional, four-connected framework structure of corner-sharing [$TO_4$] tetrahedra, where T is any tetrahedrally coordinated cation. Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum et al., *Introduction to Zeolite Science and Practice, Second Completely Revised and Expanded Edition*, Volume 137, pages 1-67, Elsevier Science, B.V., Amsterdam, Netherlands (2001).

Non-limiting examples of molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW, and SOD. Non-limiting examples of preferred molecular sieves, particularly for converting an oxygenate containing feedstock into olefin(s), include AEL, AFY, AEI, BEA, CHA, EDI, FAU, FER, GIS, LTA, LTL, MER, MFI, MOR, MTT, MWW, TAM, and TON. In one preferred embodiment, the molecular sieve of the invention has an AEI topology and/or a CHA topology, most preferably at least a CHA topology. The small, medium and large pore molecular sieves have from a 4-ring to a 12-ring or greater framework-type. In a preferred embodiment, the zeolitic molecular sieves have 8-, 10-, or 12-ring structures and an average pore size from about 3 Å to about 15 Å. In a more preferred embodiment, the molecular sieves, preferably silicoaluminophosphate (SAPO) molecular sieves, have 8-rings and are small pore molecular sieves or have an average pore size less than about 5 Å.

Molecular sieves preferably have a molecular framework of two or more corner-sharing $[TO_4]$ tetrahedral units, more preferably two or more of $[SiO_4]$, $[AlO_4]$, and $[PO_4]$ tetrahedral units. These silicon, aluminum, and/or phosphorus based molecular sieves and metal containing derivatives thereof have been described in detail in numerous publications including, for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZNAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in R. Szostak *Handbook of Molecular Sieves*, Van Nostrand Reinhold, New York, N.Y. (1992), which is herein fully incorporated by reference.

The more preferred molecular sieves include aluminophosphate (AlPO) molecular sieves and silicoaluminophosphate (SAPO) molecular sieves and substituted, preferably metal substituted, AlPO and SAPO molecular sieves. Highly preferred molecular sieves include SAPO molecular sieves and metal substituted SAPO molecular sieves. In an embodiment, the metal is an alkali metal of Group 1 of the Periodic Table of Elements, an alkaline earth metal of Group 2 of the Periodic Table of Elements, a rare earth metal of Group 3 of the Periodic Table of Elements, including the Lanthanides: lanthanum, cerium, praseodymium, neodymium, samarium, europium, gadolinium, terbium, dysprosium, holmium, erbium, thulium, ytterbium and lutetium; and scandium or yttrium, a transition metal of Groups 4 to 12 of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as $[MeO_2]$, and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and has a value from 0 to 1, preferably 0 to 0.5, and most preferably from 0 to 0.3; x, y, and z represent the mole fraction of Al, P and M as tetrahedral oxides, where M is a metal selected from one of Groups 1, 2, 3, 4, 5, 6, 7, 8, 9, 10, 11, 12, 13, 14 and Lanthanide's of the Periodic Table of Elements, preferably M is selected from one of the group consisting of Si, Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18, and AlPO-34, and metal containing derivatives thereof, such as one or a combination of SAPO-18, SAPO-34, AlPO-34, and AlPO-18, and metal containing derivatives thereof.

In an embodiment, the molecular sieve is an intergrowth material having two or more distinct crystalline phases within one molecular sieve composition. In particular, intergrowth molecular sieves are described in the U.S. patent application Ser. No. 09/924,016 filed Aug. 7, 2001 and International Publication No. WO 98/15496 published Apr. 16, 1998, both of which are herein fully incorporated by reference. For example, SAPO-18, AlPO-18, and RUW-18 have an AEI framework-type, and SAPO-34 has a CHA framework-type. Thus the molecular sieve used herein may comprise at least one intergrowth phase of AEI and CHA framework-types, especially where the ratio of CHA framework-type to AEI framework-type, as determined by the DIFFaX method disclosed in U.S. patent application Ser. No. 09/924,106 filed Aug. 7, 2001, is greater than 1:1, or preferably from about 11:9 to about 19:1 or from about 3:2 to about 10:1.

Aluminosilicate and silicoaluminophosphate molecular sieves can have a high silicon (Si) to aluminum (Al) ratio or a low silicon to aluminum ratio; however, a low Si/Al ratio is preferred for SAPO synthesis. In one embodiment where the molecular sieve is a SAPO, the molecular sieve has a Si/Al ratio less than 0.65, such as less than 0.40, for example less than 0.32, and particularly less than 0.20. In another embodiment where the molecular sieve is a SAPO, the molecular sieve has a Si/Al ratio from about 0.65 to about 0.01, such as from about 0.40 to about 0.02, for example from about 0.32 to about 0.02 or from about 0.32 to about 0.10.

The synthesis of primary molecular sieves is described in many of the references discussed above, including but not limited to U.S. Pat. Nos. 6,844,291, 6,906,232, 6,995,111, 7,166,757, 7,186,875, 7,199,277, 7,199,278, and 7,208,442, as well as U.S. Patent Application Publication Nos. 2005/0137439 and 2008/0103345, each of which are hereby incorporated by reference for their description of molecular sieve synthesis. As an example, column 7, line 15 through column 9, line 18 of U.S. Pat. No. 6,844,291 discloses such general molecular sieve synthesis details. Generally, molecular sieves are synthesized by the hydrothermal crystallization of two or more of a source of aluminum, a source of phosphorus, and a source of silicon, typically as well as a templating agent such as a nitrogen-containing organic compound. Usually, a combination of sources of silicon, aluminum, and phosphorus, optionally with one or more templating agents, is placed in a sealed pressure vessel, optionally lined with an inert plastic such as polytetrafluoroethylene, and heated under a crystallization pressure and temperature, until a crystalline material is formed. Such crystalline material can then be recovered by means known in the art, such as filtration, centrifugation, and/or decanting, to attain primary molecular sieve crystals.

The catalyst system composition can include any one of the molecular sieves previously described and one or more of the MOs described herein, optionally with a binder and/or matrix material different from the MO(s). Typically, the weight ratio of the molecular sieve to the MO(s) in the catalyst system composition can range from 5 wt % to 800 wt %, such as from 10 wt % to 600 wt %, particularly from 20 wt % to 500 wt %, and more particularly from 30 wt % to 400 wt %.

There are many different binders that can be useful in forming catalyst compositions. Non-limiting examples of binders that are useful, alone or in combination, include but are not limited to various types of hydrated alumina, silicas, and/or other inorganic oxide sols. One preferred inorganic oxide sol is aluminum chlorhydrol. The inorganic oxide sol acts like glue binding the synthesized molecular sieves and other materials (such as the matrix) together, particularly after thermal treatment. Upon heating, the inorganic oxide sol, preferably having a relatively low viscosity, can be converted into an inorganic oxide binder component. For example, an aluminum-containing sol will typically convert to an aluminum oxide binder following heat treatment.

Aluminum chlorhydrol, a hydroxylated aluminum-based sol containing a chloride counter ion, has the general formula of $Al_mO_n(OH)_oCl_p.x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7.12(H_2O)$, as is described in G. M. Wolterman et al., *Stud. Surf Sci. and Catal.*, 76, pp. 105-144 (1993), which is herein incorporated by reference. In another embodiment, one or more binders are combined with one or more other non-limiting examples of aluminum-containing materials such as aluminum oxyhydroxide, boehmite, diaspore, aluminum trihydroxide, gibbsite, bayerite, nordstrandite, doyelite, transitional aluminas (such as α-alumina, β-alumina, γ-alumina, δ-alumina, ϵ-alumina, κ-alumina, ρ-alumina, and combinations thereof), and mixtures thereof.

In another embodiment, the binder can be an aluminum-containing sol, predominantly comprising aluminum oxide, optionally including some silicon. In yet another embodiment, the binder can be peptized alumina, made by treating an alumina hydrate such as pseudobohemite with an acid, preferably with an acid that does not contain a halogen, to prepare a sol or aluminum ion solution. Non-limiting examples of commercially available colloidal alumina sols include Nalco 8676 available from Nalco Chemical Co., Naperville, Ill., and Nyacol AL20DW available from Nyacol Nano Technologies, Inc., Ashland, Mass.

Where the catalyst composition contains a matrix material, this is preferably different from the MO and any binder. Matrix materials are typically effective in reducing overall catalyst cost, acting as thermal sinks to assist in shielding heat from the catalyst composition for example during regeneration, densifying the catalyst composition, and/or increasing catalyst strength such as crush strength and attrition resistance.

Non-limiting examples of matrix materials include one or more non-active metal oxides including beryllia, quartz, silica or sols, and mixtures thereof, for example silica-magnesia, silica-zirconia, silica-titania, silica-alumina, and silica-alumina-thoria. In an embodiment, matrix materials are natural clays, such as those from the families of montmorillonite and kaolin. These natural clays can include, but are not limited to, subbentonites and those kaolins known as, for example, Dixie, McNamee, Georgia, and Florida clays. Non-limiting examples of other matrix materials include haloysite, kaolinite, dickite, nacrite, or anauxite. The matrix material, such as a clay, may be subjected to well known modification processes such as calcination and/or acid treatment and/or other chemical treatments.

In a preferred embodiment, the matrix material is a clay or a clay-type composition, particularly having a low iron and/or titania content; particularly preferably, the matrix material comprises or is kaolin. Kaolin has been found to form a pumpable, high solids content slurry, to have a low fresh surface area, and to pack together easily due to its platelet structure. A preferred average particle size of the matrix material (kaolin) is from about 0.1 μm to about 0.6 μm, with a particle size distribution such that its $D_{90}$ is less than about 1 μm.

Where the catalyst composition contains a binder or matrix material, the catalyst composition typically contains from about 1% to about 80%, such as from about 5% to about 60%, and particularly from about 5% to about 50%, by weight of the molecular sieve based on the total weight of the catalyst system composition (typically excluding the MO).

Where the catalyst composition contains both a binder and a matrix material, the weight ratio of the binder to the matrix material is typically from 1:15 to 1:5, such as from 1:10 to 1:4, and particularly from 1:6 to 1:5. The amount of binder is typically from about 2% by weight to about 30% by weight, such as from about 5% by weight to about 20% by weight, and particularly from about 7% by weight to about 15% by weight, based on the total weight of the binder, the molecular sieve, and matrix material. It has been found that a higher sieve content and lower matrix content can advantageously increase the molecular sieve catalyst composition performance, whereas a lower sieve content and higher matrix content can advantageously improve the attrition resistance.

In one embodiment, active metal oxides are those metal oxides, different from typical binders and/or matrix materials that, when used in combination with a molecular sieve in a catalyst system composition, are effective in extending of the useful life of the catalyst composition. Quantification of the extension in catalyst life can be determined by the Lifetime Enhancement Index (LEI), as defined by the following equation:

$$LEI = \frac{\text{Lifetime of Catalyst in Combination with Active Metal Oxide}}{\text{Lifetime of Catalyst}}$$

where the lifetime of the primary catalyst or catalyst system composition, in the same process under the same conditions, is the cumulative amount of feedstock processed per gram of catalyst system composition until the conversion of feedstock by the catalyst system composition falls below some defined level, for example 10%. An inactive metal oxide will have little to no effect on the lifetime of the catalyst composition, or will shorten the lifetime of the catalyst composition, and will therefore have an LEI less than or approximately equal to 1. Thus, MOs of the invention are those metal oxides, different from typical binders and/or matrix materials, that, when used in combination with a molecular sieve, provide a catalyst system composition having an LEI greater than 1. By definition, a molecular sieve catalyst composition that has not been combined with an MO (primary molecular sieve catalyst, optionally including a matrix and/or a binder) should have an LEI approximately equal to 1.0.

It has been found that, by including an MO in combination with a primary molecular sieve catalyst, a catalyst system composition can be produced having an LEI from 1.1 to 20, such as from about 1.5 to about 10. Typically catalyst system compositions according to the invention can exhibit LEI values of at least 1.2, for example from about 1.2 to 15, and more particularly greater than 1.3, such as greater than 1.5, greater than 1.7, or greater than 2.

A number of metal oxides have been identified as useful in acting as co-catalysts when used along with SAPO and other small pore molecular sieve catalysts (primary catalysts) in OTO (MTO) processes. Generally speaking, the identified benefits can include, but are not limited to, lower production of coke (coke make) and/or longer primary catalyst lifetime (defined as the amount of methanol feed that can be converted before the catalyst deactivates, normalized by the amount of active catalyst present), which is often referred to as Cumulative Methanol Converted Per gram of Sieve (CMCPS). Catalyst lifetime, as used herein, refers to the lifetime of the catalyst system, which includes the primary molecular sieve catalyst as well as any MO co-catalyst, if present.

The surface area of each MO sample is measured in accordance with the method of Brunauer, Emmett, and Teller (BET), published as ASTM D 3663. In one embodiment, the MO has a BET surface area of at least 10 $m^2/g$, such as from greater than 10 $m^2/g$ to about 300 $m^2/g$. In another embodiment, the MO has a BET surface area of at least 20 $m^2/g$, such as from 20 $m^2/g$ to 250 $m^2/g$. In yet another embodiment, the MO has a BET surface area of at least 25 $m^2/g$, such as from 25 $m^2/g$ to about 200 $m^2/g$, or of at least 30 $m^2/g$.

Potentially useful MOs can include, but are not limited to, oxides of metals from Groups 2, 3, and/or 4 from the Periodic Table of Elements using the IUPAC format described in the *CRC Handbook of Chemistry and Physics,* 78th Edition, CRC Press, Boca Raton, Fla. (1997), as well as Lanthanides, Actinides, and mixtures/combinations thereof, preferably yttrium oxides, lanthanum-zirconium oxides, magnesium oxides, and mixtures/combinations thereof. For instance, some samples of yttria have been found to be virtually inactive as co-catalysts, while, on the other hand, other samples have been found to be quite effective.

There are many ways of making a catalyst system composition according to the invention. In one embodiment, the molecular sieve is first formed and is then physically mixed with the MO, preferably in a substantially dry, dried, or calcined state. As an example, column 14, line 24 through column 15, line 50 of U.S. Pat. No. 6,844,291 discloses general details for making catalyst system compositions containing primary molecular sieve catalysts and active metal oxides. In the aforementioned embodiment, the primary molecular sieve and MO co-catalyst are preferably physically mixed in their calcined state. Without being bound by any particular theory, it is believed that intimate mixing of the molecular sieve and the MO(s) can improve conversion processes using the catalyst system compositions of the invention. Intimate mixing can be achieved by any method known in the art, such as mixing with a mixer, muller, drum mixer, ribbon/paddle blender, kneader, or the like. Chemical reaction between the molecular sieve and the MO(s) is believed to be unnecessary and, in general, is not preferred. Alternately, in other embodiments, the primary molecular sieve catalyst can be formulated with the binder and/or matrix, if present, separately from the calcined MO, e.g. such that the molecular sieve catalyst and MO are present in different particles or, at best, are agglomerated on the surfaces of each others' respective particles. As an example, column 12, line 38 through column 13, line 11 of U.S. Pat. No. 7,166,757 discloses such general details for making catalyst system compositions containing molecular sieve catalysts and active metal oxides.

In addition to specifying the chemical identity of an MO co-catalyst, the method by which these materials are activated can be very important. In particular, calcining the materials at different conditions can lead to a wide range of effectiveness. For example, increasing the calcination temperature from 600° C. to 1000° C. can lead to a decrease in effectiveness, in some cases as much as a three-fold decrease. As a result, the calcination temperature of the MO (or metal-containing precursor, if the MO is made by calcining a metal precursor to form the MO) can be below about 1050° C., preferably below about 950° C., below about 850° C., below about 750° C., or below about 650° C. The minimum calcination temperature of the MO (or metal-containing precursor, if the MO is made by calcining a metal precursor to form the MO) needs to be high enough to convert any non-oxide material to its oxide form, which will depend on the metal to be oxidized (and/or the nature of any precursor or other material). In one embodiment, the calcination temperature can be at least about 250° C., preferably at least about 300° C., at least about 350° C., at least about 400° C., at least about 450° C., at least about 500° C., at least about 550° C., or at least about 600° C.

It has been found that the number/density of basic sites on such co-catalysts can be measured more accurately by titration with nitromethane than with other, previously-used techniques.

Additionally, it has been found that the effectiveness of the calcined MO may be well correlated with a Loading Index ("LI"), which is defined as the product of the wt % MO on active sieve and the total surface area ("SA") in $m^2/g$. The SA can advantageously be measured by the well-known BET method. As used herein, wt % MO is defined by how much MO is added to the primary molecular sieve catalyst and not relative to the total of the base and the MO. For example, 2 grams MO plus 10 grams sieve is reported herein as 20 wt % (2/10) loading and not as 16.7 wt % (2/(2+10)).

Without being bound by theory, it is also believed that MO crystal structure may significantly affect its performance as co-catalyst in OTO conversion reactions. For example, yttria MOs having a monoclinic crystal structure after calcination tend to have drastically lower activities and/or LEIs (when combined with the aforementioned primary molecular sieve catalysts) than yttria MOs having a cubic crystal structure after calcination. This crystal structure effect can be so pronounced, for example in yttria MOs, that it may not be limited to post-calcination crystal structure. Indeed, even a pre-calcined yttria MO having a monoclinic crystal structure that changes to a cubic crystal structure upon calcination is still believed to exhibit a lower activity and/or LEI (when combined with the aforementioned primary molecular sieve catalysts) than a yttria MO having a pre-calcination and post-calcination cubic crystal structure.

In a preferred embodiment of the process of the invention, the feedstock contains one or more oxygenates, more specifically one or more organic compound(s) containing at least one oxygen atom. In a particularly preferred embodiment, the oxygenate in the feedstock comprises or is one or more alcohols, preferably aliphatic alcohols where the aliphatic moiety has from 1 to 20 carbon atoms, preferably from 1 to 10 carbon atoms, more preferably from 1 to 4 carbon atoms. The alcohols useful as feedstock can advantageously include lower straight and branched chain aliphatic alcohols and their unsaturated counterparts.

Non-limiting examples of oxygenates in feedstock include, but are not limited to, methanol, ethanol, n-propanol, isopropanol, methyl ethyl ether, dimethyl ether, diethyl ether, di-isopropyl ether, formaldehyde, acetaldehyde, propionaldehyde, dimethyl carbonate, dimethyl ketone, acetic acid, and mixtures thereof. In a preferred embodiment, the feedstock comprises predominantly methanol, ethanol, dimethyl ether, diethyl ether, or a combination thereof, more preferably comprises predominantly methanol and/or dimethyl ether, and most preferably comprises predominantly methanol.

The various oxygenate feedstocks discussed above, particularly those containing alcohol(s), can be converted primarily into one or more olefins. The olefins produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

The catalyst system composition is particularly useful in the process that is generally referred to as the gas-to-olefins (GTO) process or alternatively, the methanol-to-olefins (MTO) process. In this process, an oxygenated feedstock, preferably a methanol-containing feedstock, is converted in the presence of a molecular sieve catalyst composition into one or more olefins, preferably and predominantly, ethylene and/or propylene.

Using the catalyst composition of the invention for the conversion of an oxygenate feedstock, the amount of olefins produced based on the total weight of hydrocarbon produced can advantageously be greater than 50 wt %, typically greater than 60 wt %, such as greater than 70 wt %, preferably greater than 80 wt %. Moreover, the amount of ethylene and/or propylene produced based on the total weight of hydrocarbon product produced can advantageously be greater than 40 wt %, typically greater than 50 wt %, for example greater than 65 wt %, preferably greater than 75 wt % or greater than 78 wt %. Typically, the amount ethylene produced in weight percent based on the total weight of hydrocarbon product produced, can advantageously be greater than 20 wt %, such as greater than 30 wt %, for example greater than 35 wt % or greater than 40 wt %. In addition, the amount of propylene produced in weight percent based on the total weight of hydrocarbon product produced can advantageously be greater than 20 wt %, such as greater than 25 wt %, for example greater than 30 wt %, and preferably greater than 35 wt %.

Using the catalyst system composition of the invention for the conversion of a feedstock comprising methanol and/or dimethylether to ethylene and propylene, it has been found that the production of saturates such as ethane and propane can be reduced by greater than 10%, such as greater than 20%, for example greater than 30%, and particularly in the range of from about 30% to 40% compared to a similar catalyst composition at the same conversion conditions but without the MO component.

In addition to the oxygenate component, such as methanol, the feedstock may contain one or more diluents, which are generally non-reactive to the feedstock or molecular sieve catalyst composition and are typically used to reduce the concentration of the feedstock. Non-limiting examples of diluents can include helium, argon, nitrogen, carbon monoxide, carbon dioxide, water, essentially non-reactive paraffins (especially alkanes such as methane, ethane, and propane), essentially non-reactive aromatic compounds, and mixtures thereof. When present, the most preferred diluents are water and/or nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve and/or co-catalyst.

The OTO process can be conducted over a wide range of temperatures, such as from about 200° C. to about 1000° C., for example from about 250° C. to about 800° C., including from about 250° C. to about 750° C., conveniently from about 300° C. to about 650° C., typically from about 350° C. to about 600° C., and particularly from about 350° C. to about 550° C.

Similarly, the OTO process can be conducted over a wide range of pressures, including autogenous pressure. Typically, the partial pressure of the feedstock, exclusive of any diluent therein employed in the process, can be from about 0.1 kPaa to about 5 MPaa, such as from about 5 kPaa to about 1 MPaa or from about 20 to about 500 kPaa.

The weight hourly space velocity (WHSV), defined as the total weight of feedstock, excluding any diluent(s), per hour per weight of molecular sieve in the catalyst system composition, can ranges from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 hr to about 1000 $hr^{-1}$. In one embodiment, the WHSV can be greater than 20 $hr^{-1}$ and, where the feedstock contains methanol and/or dimethyl ether, can advantageously be from about 20 $hr^{-1}$ to about 300 $hr^{-1}$.

Where the OTO process is conducted in a reactor containing a fluidized bed, the superficial gas velocity (SGV) of the feedstock including diluent and reaction products within the reactor system, and particularly within a riser reactors, can be at least 0.1 meter per second (m/sec), such as greater than 0.5 m/sec or greater than 1 m/sec, for example greater than 2 m/sec, conveniently greater than 3 m/sec or greater than 4 m/sec. See, for example, U.S. patent application Ser. No. 09/708,753, filed Nov. 8, 2000, which is herein incorporated by reference, for a more complete description of SGV in OTO riser reactors.

The OTO process of the invention can conveniently be conducted as a fixed bed process, though more typically as a fluidized bed process (including a turbulent bed process), such as a continuous fluidized bed process, and particularly a continuous high velocity fluidized bed process.

The OTO process can additionally or alternately take place in a variety of catalytic reactors such as hybrid reactors having dense or fixed bed reaction zones and/or fast fluidized bed reaction zones coupled together, circulating fluidized bed reactors, riser reactors, and the like. Suitable conventional reactor types are described, for example, in U.S. Pat. Nos. 4,076,796 and 6,287,522 (dual riser), and in *Fluidization Engineering*, D. Kunii and O. Levenspiel, Robert E. Krieger Publishing Company, New York, N.Y. (1977), which are all herein incorporated by reference for their disclosures of reactors.

Some preferred reactor types are those generally described in *Riser Reactor, Fluidization and Fluid-Particle Systems*, pp. 48-59, F. A. Zenz and D. F. Othmo, Reinhold Publishing Corporation, New York, 1960, in U.S. Pat. No. 6,166,282 (fast-fluidized bed reactor), and in U.S. patent application Ser. No. 09/564,613, filed May 4, 2000 (multiple riser reactor), which are all herein incorporated by reference for their reactor disclosures.

In one practical embodiment, the OTO process can be conducted as a fluidized bed process or high velocity fluidized bed process utilizing a reactor system, a regeneration system, and a recovery system. In such an embodiment, the reactor system could conveniently include a fluid bed reactor system having a first reaction zone within one or more riser reactors and a second reaction zone within at least one disengaging vessel, typically comprising one or more separators (such as cyclones). In one aspect of this embodiment, the one or more riser reactors and disengaging vessel can be contained within a single reactor vessel. Fresh feedstock, optionally with one or more diluents, can be fed to the riser reactor(s) into which the catalyst system composition (or coked version thereof) is or has been introduced. In one aspect of this embodiment, prior to being introduced to the riser reactor(s), the catalyst system composition (or coked version thereof) can be contacted with a liquid (preferably water or methanol) and/or a gas (e.g. inert, such as nitrogen).

In an embodiment, the amount of fresh oxygenate feedstock fed as a liquid and/or a vapor to the reactor system can be from 0.1 wt % to about 85 wt %, such as from about 1 wt % to about 75 wt %, more typically from about 5 wt % to about 65 wt %, based on the total weight of the feedstock including any diluent contained therein.

The feedstock entering the reactor system can preferably be converted (partially or fully) in the first reactor zone into a gaseous effluent that enters the disengaging vessel along with the coked catalyst composition. In a preferred embodiment, the separator(s) can be provided within the disengaging vessel to separate the coked catalyst composition from the gaseous effluent containing one or more olefins within the disengaging vessel. Although cyclones are preferred, gravity effects within the disengaging vessel can also be used to separate the catalyst composition from the gaseous effluent. Other methods for separating the catalyst composition from the gaseous effluent can include but are not limited to the use of plates, caps, elbows, and the like.

In one embodiment, the disengaging vessel can include a stripping zone, typically located in a lower portion. In the stripping zone, the coked catalyst composition can be contacted with a gas, preferably one or a combination of steam, methane, carbon dioxide, carbon monoxide, hydrogen, and an inert gas such as argon (preferably including steam) to recover associated (adsorbed) hydrocarbons from the coked catalyst composition that can then be introduced to the regeneration system. The regeneration system can comprise a regenerator where the coked catalyst composition is contacted with a regeneration medium, preferably a gas containing oxygen, under conventional regeneration conditions of temperature, pressure, and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide, and/or hydrogen. Suitable regeneration conditions are generally those capable of burning coke from the coked catalyst composition, preferably to a level less than 1 wt % (or in some cases 0.5 wt %), based on the total weight of the coked catalyst composition entering the regeneration system. For example, the regeneration temperature may be from about 200° C. to about 1500° C., such as from about 300° C. to about 1000° C., for example from about 450° C. to about 750° C., and conveniently from about 550° C. to about 700° C. The regeneration pressure may be from about 15 psia (103 kpaa) to about 500 psia (3448 kpaa), such as from about 20 psia (138 kpaa) to about 250 psia (1724 kpaa), including from about 25 psia (172 kPaa) to about 150 psia (1034 kpaa), and conveniently from about 30 psia (207 kpaa) to about 60 psia (414 kpaa).

The residence time of the catalyst composition in the regenerator may be from about one minute to about several hours, such as from about 1 to 100 minutes, and the volume of oxygen in the regeneration gas may be from about 0.01 mol % to about 5 mol % based on the total volume of the gas.

The burning of coke in the regeneration step is an exothermic reaction, and in a particular embodiment, the temperature within the regeneration system can be controlled by various techniques in the art, including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in this embodiment, can be a heat exchanger located either internal or external to the regeneration system. Other methods for operating a regeneration system are disclosed in U.S. Pat. No. 6,290,916 (controlling moisture), which is herein fully incorporated by reference.

The regenerated catalyst composition withdrawn from the regeneration system, preferably from a catalyst cooler, can be combined with a fresh catalyst system composition, a recirculated catalyst system composition, additional feedstock, and/or fresh gases or liquids, and returned to the riser reactor(s). In one embodiment, the regenerated catalyst composition withdrawn from the regeneration system can be returned to the riser reactor(s) directly, preferably after passing through a catalyst cooler. A carrier, such as an inert gas, feedstock vapor, steam, or the like, may be used, semi-continuously or continuously, to facilitate the introduction of the regenerated catalyst composition back into the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, Experimental Techniques, Circulating Fluidized Beds, Grace, Avidan and Knowlton, eds., Blackie, 1997 (336-337), which is herein incorporated by reference.

Coke levels on the catalyst composition can be measured by withdrawing the catalyst composition from the conversion process and determining its carbon content. Typically when SAPO molecular sieves are used as the primary catalyst, the conversion process can be controlled so that the coke level immediately prior to regeneration is between about 8 weight percent and about 20 weight percent, such as from about 13 weight percent to about 18 weight percent, based on the weight of the molecular sieve. Typical levels of coke on the molecular sieve catalyst composition after regeneration are in the range of from 0.02 wt % to about 10 wt %, such as from about 0.02 wt % to about 5 wt % or from about 0.3 wt % to about 2 wt %, based on the weight of the molecular sieve.

The gaseous effluent can be withdrawn from the disengaging system and then passed through a recovery system. There are many well known recovery systems, techniques, and sequences that can be useful in separating/purifying olefins from the gaseous effluent. Recovery systems generally comprise one or more or a combination of various separation, fractionation, and/or distillation towers, columns, splitters, or trains, reaction systems such as ethylbenzene manufacture (U.S. Pat. No. 5,476,978) and other derivative processes such as aldehyde, ketone, and ester manufacture (U.S. Pat. No. 5,675,041), and other associated equipment, for example various condensers, heat exchangers, refrigeration systems or chill trains, compressors, knock-out drums or pots, pumps, and the like.

Non-limiting examples of these towers, columns, splitters, and trains used alone or in combination can include one or more of a demethanizer, preferably a high temperature demethanizer, a deethanizer, a depropanizer, a wash tower (often referred to as a caustic wash tower and/or quench tower), absorbers, adsorbers, membranes, ethylene ($C_2^{=}$) splitter, propylene ($C_3^{=}$) splitter, butene ($C_4^{=}$) splitter, and the like.

Various recovery systems useful for recovering predominantly olefins, preferably light olefins such as ethylene, propylene, and/or butene, more preferably at least prime olefins (i.e., ethylene and/or propylene), are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Other recovery systems that include purification systems, for example for the purification of olefins, are described in Kirk-Othmer *Encyclopedia of Chemical Technology,* 4th Edition, Volume 9, John Wiley & Sons, 1996, pages 249-271 and 894-899, which is herein incorporated by reference. Purification systems are also described, for example, in U.S. Pat. No. 6,271,428 (purification of a diolefin hydrocarbon stream), U.S. Pat. No. 6,293,999 (separating propylene from propane), and U.S. patent application Ser. No. 09/689,363, filed Oct. 20, 2000 (purge stream using hydrating catalyst), which are herein incorporated by reference.

Generally accompanying most recovery systems is the production, generation, or accumulation of (less preferred and/or undesirable) additional products, by-products, and/or contaminants along with the preferred/desirable products. The preferred products, the prime olefins, such as ethylene and propylene, are typically purified for use in derivative manufacturing processes such as polymerization processes. Therefore, in a particularly preferred embodiment of the recovery system, the recovery system also includes a prime olefin purification system. For example, the prime olefins produced particularly in a MTO process can be passed through a purification system that removes low levels of by-products/contaminants.

Non-limiting examples of contaminants/by-products can include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants and/or by-products can include hydrogen and hydrocarbons such as acetylene, methyl acetylene, propadiene, butadiene, and butyne.

Typically, in converting oxygenates to olefins having 2 or 3 carbon atoms, a minor amount hydrocarbons, particularly olefins, having 4 or more carbon atoms is also produced. The amount of $C_{4+}$ hydrocarbons is normally less than 20 wt %, such as less than 10 wt %, for example less than 5 wt %, and particularly less than 2 wt %, based on the total weight of the effluent gas withdrawn from the process, excluding water. Typically, therefore the recovery system may include one or more reaction systems for converting the $C_{4+}$ impurities to useful products.

Non-limiting examples of such reaction systems are described in U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and J. Cosyns et al., Process for Upgrading $C_3$, $C_4$ and $C_5$ Olefinic Streams, *Pet. & Coal*, Vol. 37, No. 4 (1995) (dimerizing or oligomerizing propylene, butylene and pentylene), which are all herein fully incorporated by reference.

The preferred light olefins produced by any one of the processes described above are typically high purity prime olefin products that contain a single carbon number olefin in an amount greater than 80 wt %, such as greater than 90 wt %, such as greater than 95 wt %, for example at least about 99 wt %, based on the total weight of the olefin.

In one practical embodiment, the process of the invention can form part of an integrated process for producing light olefins from a hydrocarbon feedstock, preferably a gaseous hydrocarbon feedstock, particularly methane and/or ethane. The first step in the process can include passing the gaseous feedstock, preferably in combination with a water stream, to a syngas production zone to produce a synthesis gas (syngas) stream, typically comprising carbon dioxide, carbon monoxide, and hydrogen. Syngas production is well known, and typical syngas temperatures can be from about 700° C. to about 1200° C. and syngas pressures can be from about 2 MPa to about 100 MPa. Synthesis gas streams are generally produced from natural gas, petroleum liquids, and carbonaceous materials such as coal, recycled plastic, municipal waste, or other organic materials. In one preferred embodiment, synthesis gas streams can be produced via steam reforming of natural gas.

The next step in the process can involve contacting the synthesis gas stream generally with a heterogeneous catalyst, typically a copper based catalyst, to produce an oxygenate-containing stream, often in combination with water. In one embodiment, the contacting step can be conducted at a temperature from about 150° C. to about 450° C. and at a pressure from about 5 MPa to about 10 MPa.

This oxygenate-containing stream, or crude methanol, typically contains the alcohol product and various other components such as ethers, particularly dimethyl ether, ketones, aldehydes, dissolved gases such as hydrogen, methane, carbon oxides, and nitrogen, and fuel oil. The oxygenate-containing stream, crude methanol in the preferred embodiment, can be passed through a well known purification processes (e.g., distillation, separation, and/or fractionation), resulting in a purified oxygenate containing stream, for example, commercial Grade A and/or AA methanol.

The oxygenate-containing stream or purified oxygenate containing stream, optionally with one or more diluents, can then be used as a feedstock in a process to produce light olefins, such as ethylene and/or propylene. A non-limiting example of this integrated process is described in EP-B-0 933 345, which is herein fully incorporated by reference.

In another more fully integrated process that optionally is combined with the integrated processes described above, the olefin(s) produced can be directed to, in one embodiment, one or more polymerization processes for producing various olefin-containing polymers/co-polymers (see, for example, U.S. patent application Ser. No. 09/615,376, filed Jul. 13, 2000, which is herein fully incorporated by reference.)

Olefin-based polymerization processes can include, but are not limited to, solution, gas phase, slurry phase, and high pressure processes, or a combination thereof. Particularly preferred is a gas phase or a slurry phase polymerization of one or more olefin monomers, at least one of which is ethylene or propylene, optionally including one or more other polymerizable comonomers. These polymerization processes can advantageously utilize a polymerization catalyst that can include any one or a combination of the molecular sieve catalysts discussed above; however, preferred polymerization catalysts can include Ziegler-Natta, Phillips-type, metallocene, metallocene-type, and advanced polymerization catalysts, and mixtures thereof.

In a preferred embodiment, the integrated process comprises a process for polymerizing one or more olefins, optionally in the presence of a polymerization catalyst system, in a polymerization reactor to produce one or more olefin-containing polymer products, wherein the one or more olefins have been made by converting an oxygenate (such as an alcohol, particularly methanol) using a molecular sieve catalyst composition as described above. One preferred polymerization catalyst system is a supported metallocene catalyst system, which can comprises a support, a metallocene or metallocene-type compound, and an activator, which can preferably include (or be) a non-coordinating anion or alumoxane, or combination thereof (more preferably the activator comprises or is alumoxane).

The (co)polymers produced by the polymerization processes described above can include, but are not limited to, linear low density polyethylene, elastomers, plastomers, high density polyethylene, low density polyethylene, polypropylene, and polyethylene and/or polypropylene copolymers. The (co)polymers produced by the polymerization processes can be atactic, isotactic, syndiotactic, or a combination thereof, and can also include random, block (diblock, triblock, multiblock, or the like), alternating, impact, or other copolymers. The one or more olefins can additionally or alternately be copolymerized with diolefins or other crosslinking/crosslinkable monomers to form branched, comb, star, or other copolymers.

Additionally or alternately, the present invention can be described with reference to the following embodiments.

Embodiment 1

A process for converting an oxygenate-containing feed into an olefin-containing product, the process comprising: (a) providing, as a co-catalyst, an oxide of at least one metal selected from the group consisting of Groups 2, 3, and 4 of the Periodic Table of Elements, Lanthanides, Actinides, and combinations thereof; (b) contacting the metal oxide with nitromethane under conditions sufficient for the nitromethane to adsorb onto the metal oxide; (c) analyzing the nitromethane-adsorbed metal oxide using NMR to determine a basic site density of the metal oxide; (d) providing a catalyst system comprising a primary catalyst selected from the group consisting of aluminosilicates, aluminophosphates, silicoaluminophosphates, metal-containing derivatives thereof, and combinations thereof, and the metal oxide as a co-catalyst, wherein the basic site density of the metal oxide is at least 0.085 mmol/g, and wherein the metal oxide has a BET surface area of at least 20 $m^2/g$ (and, when the metal oxide comprises yttria, preferably a cubic crystal structure); (e) contacting the oxygenate-containing feedstock with the catalyst system under conditions sufficient to form an olefin-containing product; and (f) separating the olefin-containing product into at least ethylene and/or propylene.

Embodiment 2

The process of embodiment 1, wherein the metal oxide has a BET surface area of at least 30 $m^2/g$, preferably at least 40 $m^2/g$.

Embodiment 3

The process of embodiment 1 or embodiment 2, wherein the oxygenate-containing feedstock comprises methanol and/or dimethylether.

Embodiment 4

The process of any of the previous embodiments, wherein, prior to contact with the nitromethane, the metal oxide is calcined at a temperature from 250° C. to 1050° C., preferably from 300° C. to 950° C.

Embodiment 5

The process of any of the previous embodiments, wherein the basic site density of the metal oxide is at least 0.10 mmol/g, preferably at least 0.15 mmol/g.

Embodiment 6

The process of any of the previous embodiments, wherein the primary catalyst is an aluminosilicate having a ratio of $Si/Al_2$ from 80 to 5000, preferably from 100 to 4000.

Embodiment 7

The process of any of embodiments 1-5, wherein the primary catalyst is a silicoaluminophosphate having a CHA framework type, an AEI framework type, or a combination or intergrowth thereof.

Embodiment 8

The process of any of embodiments 1-5 and 7, wherein the primary catalyst is a silicoaluminophosphate having an empirical formula, on an anhydrous basis, of $Si_xAl_yP_zO_2$, wherein x is from greater than 0 to 0.25, y is from 0.4 to 0.5, and z is from 0.25 to 0.5.

Embodiment 9

A process for forming an olefin-containing polymer and/or oligomer, comprising: (a) converting an oxygenate-containing feed into an olefin-containing product according to the process of any of the previous embodiments; and (b) oligomerizing and/or polymerizing the ethylene and/or propylene separated from the olefin-containing product, optionally in conjunction with one or more olefin-forming catalysts, and optionally along with one or more additional comonomers, under conditions sufficient to form the olefin-containing polymer and/or oligomer.

Embodiment 10

A method for determining basic site density in a metal oxide co-catalyst for use in an oxygenate-to-olefins conversion reaction, the method comprising: (a) providing an oxide of at least one metal selected from the group consisting of Groups 2, 3, and 4 of the Periodic Table of Elements, Lanthanides, Actinides, and combinations thereof; (b) contacting the metal oxide with nitromethane under conditions sufficient for the nitromethane to adsorb onto the metal oxide; (c) analyzing the nitromethane-adsorbed metal oxide using NMR to determine a basic site density of the metal oxide; and (d) determining if the basic site density is sufficient to indicate that the metal oxide would be useful as a co-catalyst in an oxygenate-to-olefins conversion reaction.

Embodiment 11

The method of embodiment 10, wherein the metal oxide comprises yttria having a cubic crystal structure.

Embodiment 12

The method of embodiment 10 or embodiment 11, wherein the metal oxide has a BET surface area of at least 20 $m^2/g$, preferably at least 30 $m^2/g$, for example at least 40 $m^2/g$.

Embodiment 13

The method of any of embodiments 10-12, wherein, prior to contact with the nitromethane, the metal oxide is calcined at a temperature of at least 250° C., preferably at least 300° C.

Embodiment 14

The method of any of embodiments 10-13, wherein, prior to contact with the nitromethane, the metal oxide is calcined at a temperature below 1050° C., preferably below 950° C.

EXAMPLES

The following Examples have been included as a tool to help exemplify certain aspects of the present invention but not to define the patentable scope of the invention, as recited in the claims below.

Example 1

As can be seen from Table 1, both the SA and nitromethane-titrated number of basic sites of certain yttria MOs tend to decrease with increasing calcination temperature.

TABLE 1

| Yttria MO Sample | $T_{Calcination}$ ° C. | SA (by BET) $m^2/g$ | Basic Sites (by $CH_3NO_2$) mmol/g |
|---|---|---|---|
| 1 | 600 | 69 | 0.34 |
| 2 | 800 | 52 | 0.16 |
| 3 | 1000 | 25 | 0.09 |
| 4 | 1000 | — | 0.04 |

Samples 1-3 in Table 1 above were made according to the following procedure. About 200 grams of yttrium nitrate [$Y(NO_3)_3.6H_2O$] was dissolved in about 2000 mL water while stirring. The pH was adjusted to about 9 (measured by pH-strips) using $NH_4OH$ (about 25 wt % in water), added dropwise (about 2 drops per second). About 173 mL $NH_4OH$ was added. The liquid turned turbid and viscous during the addition. The slurry was then transferred into an autoclave, which was heated to about 100° C. (about 4 hours heating time), and was maintained for approximately 72 hours under quiescent conditions. The product was recovered by centrifugation (about 4000 rpm; 1×60 minutes; 4×30 minutes), re-suspended in ethanol, and dried at about 60° C. for about 48 hours. The yield was approximately 80 grams. Roughly 10-gram portions were used for the calcination experiments in Table 1 (Examples 1-3), where the calcinations were conducted by heating the respective samples to their respective given temperatures at a heating rate of about 2° C./min, and then holding them approximately at each given temperature for about 3 hours under flowing air atmosphere. Sample 4 was obtained from Aldrich in its calcined form.

The basicity of the MO is important in that two samples of nominally the same MO can have significantly different number of basic sites and, as a consequence of this difference, can have significant differences in the ability to influence the OTO reaction chemistry, specifically with respect to extending the catalyst lifetime. This effect is illustrated in Table 2 below.

Mixing the MO co-catalyst with the primary molecular sieve catalyst (which, in this case, preferably has a CHA and/or AEI framework type, and/or preferably is SAPO-34, SAPO-18, or a combination or intergrowth thereof) can advantageously produce a catalyst system that has a longer lifetime than the primary molecular sieve catalyst alone, when used to convert a methanol-containing feed into light olefins (ethylene and/or propylene) under MTO conditions. This “longer lifetime” can be quantified by using a Lifetime Extension Index (LEI), which is defined herein as the percent increase in catalyst system lifetime over the lifetime of the catalyst system without the MO co-catalyst under the same process conditions.

Table 2 illustrates two important effects of adding a yttria MO co-catalyst to a base MTO molecular sieve catalyst. The first is that adding different amounts of MO (wt % on sieve) can significantly impact the LEI. Secondly, the calcination temperature of the yttria at any given loading can also affect the LEI—higher calcination temperatures can tend to lead to lower surface area and/or to reduced improvements in LEIs.

TABLE 2

| Sample | $T_{Calcination}$ (for MO) [° C.] | $Y_2O_3$ content [wt % on Sieve] | SA (by BET) [m²/g] | Average Catalyst Life [grams feed converted per gram sieve] | LEI (% CMCPS Increase) [Lifetime/ Lifetime (base cat-100%)] |
|---|---|---|---|---|---|
| 5 | N/A | 0 | N/A | 23.4 | 0% (base) |
| 6 | 600 | 10 | 69 | 62.2 | 166% |
| 7 | 800 | 10 | 52 | 51.1 | 118% |
| 8 | 1000 | 10 | 25 | 37.7 | 61% |
| 9 | 600 | 30 | 69 | 130 | 456% |
| 10 | 800 | 30 | 52 | 100 | 327% |
| 11 | 1000 | 30 | 25 | 70 | 199% |

Example 2

As the additional experiments shown in Table 3 illustrate, the product of wt % MO loading and SA, defined as LI in Eq. 1 above, can be used to describe the combined effect of the two variables on LEI, and, as can also be seen from the results in Table 3, benefits can be observed over a wide range of wt % MO loadings and SAs. This observation can also be viewed graphically in FIG. 1 using the data in Table 3.

Specifically, the lifetime of the catalyst system in OTO (particularly in MTO) processes can be controlled by varying either the MO loading or the SA of a MO co-catalyst added to a primary OTO molecular sieve catalyst. The SA of the MO can be seen to correlate relatively well with the basicity of the MO, as measured by nitromethane titration, and can be controlled using a number of variables, e.g. by varying the temperature at which the MO is calcined. Using the basicity measurement can advantageously provide a way of distinguishing between potentially useful MO co-catalysts having nominally similar compositions but yet having significantly different impacts on the lifetimes of the OTO catalyst systems.

TABLE 3

| Sample | $T_{Calcination}$ (for MO) [° C.] | MO Loading [wt % on Sieve] | MO SA (by BET) [m²/g] | LI SA * Loading | Average Catalyst Life [grams feed converted per gram sieve] | LEI (% CMCPS Increase) [Lifetime/ Lifetime (base cat-100%)] |
|---|---|---|---|---|---|---|
| 12 | 600 | 10% | 69 | 6.9 | 60.1 | 156% |
| 13 | 600 | 10% | 69 | 6.9 | 64.2 | 174% |
| 14 | 800 | 10% | 52 | 5.2 | 52.2 | 123% |
| 15 | 800 | 10% | 52 | 5.2 | 49.9 | 113% |
| 16 | 1000 | 10% | 25 | 2.5 | 34.4 | 47% |
| 17 | 1000 | 10% | 25 | 2.5 | 40.9 | 74% |
| 18 | 600 | 30% | 69 | 20.7 | 86.4 | 269% |
| 19 | 600 | 30% | 69 | 20.7 | 74.6 | 218% |
| 20 | 800 | 30% | 52 | 15.6 | 78.3 | 234% |
| 21 | 8000 | 30% | 52 | 15.6 | 79.3 | 239% |
| 22 | 1000 | 30% | 25 | 7.5 | 66.6 | 184% |
| 23 | 1000 | 30% | 25 | 7.5 | 62.8 | 168% |
| 24 | 600 | 50% | 69 | 34.5 | 142.3 | 507% |
| 25 | 600 | 100% | 69 | 69 | 143.4 | 512% |
| 26 | 600 | 200% | 69 | 138 | 185.9 | 693% |
| 27 | N/A | 0% | N/A | N/A | 23.6 | 1% |
| 28 | N/A | 0% | N/A | N/A | 23.3 | −1% |
| 29 | N/A | 0% | N/A | N/A | 23.4 | 0% |

Example 3

NMR measurement of MO basic site density. MO basic site density can be measured using a solid-state nuclear magnetic resonance method. Sample preparation can be rather important in NMR measurement of basic sites of MO samples. In the present case, MOs were activated using a shallow bed CAVERN device. Please refer to the following prior publication for operational details on using CAVERN apparati for this purpose: Xu, T., and Haw, J. F., *Top. Catal.,* 1997, 4, 109-118. A thin layer of each MO sample was spread out in a CAVERN device, and the temperature of the MO layer was raised under sub-atmospheric pressure (e.g., vacuum of about 0.13 kPa or less). The MO co-catalyst was typically held at the desired temperature for about 2 hours under the sub-atmospheric pressure (vacuum) prior to adsorption of nitromethane-$^{13}C$ at ambient temperature (approximately 20-25° C.).

After nitromethane adsorption, the sample was loaded into a 5-mm NMR rotor, and the rotor was sealed with a Kel-F end cap via manipulation of the CAVERN device. All the operations were performed while the sample was still under the sub-atmospheric pressure (vacuum), ensuring sample integrity for the NMR study. After the desired NMR spectra were acquired, the weight of the rotor, the catalyst, and the end cap were determined, followed by weight determination of the rotor and the end cap upon unpacking of the sample. The difference in the sums of the weights represented the amount of the MO in the rotor.

$^{13}C$ NMR experiments were performed on a 400 MHz solid state NMR spectrometer, operating at 100 MHz for $^{13}C$. Quantitative $^{13}C$ Bloch Decay spectra were represented as the average of about 100-400 scans and at about 10-40 sec pulse delay. All the reported chemical shifts were referenced to tetramethylsilane (TMS) at 0 ppm.

Example 4

Measuring Basic Site Density with $^{13}C$ NMR of Nitromethane-$^{13}C$.

The acidity of protons on nitromethane is relatively weak (pKa ~10 in aqueous solution; orders of magnitudes less acidic than a typical organic acid such as acetic acid). The strong basic sites on a MO can react with nitromethane to form an aci-anion as shown in Scheme 1 below. Since one basic site is consumed for the formation of every aci-anion, the density of basic sites on MOs can be quantified by counting the number of aci-anions.

Scheme 1. A simplified reaction scheme illustrating the formation of aci-anion from nitromethane reacting on a basic site of a MO such as $Y_2O_3$.

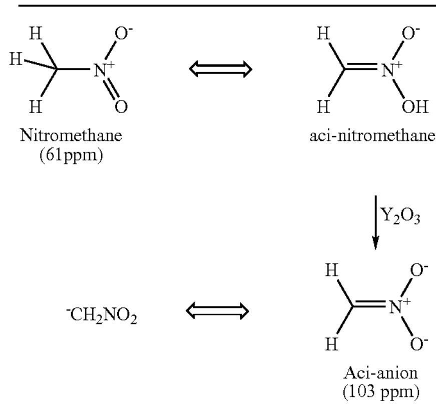

Figure 2:
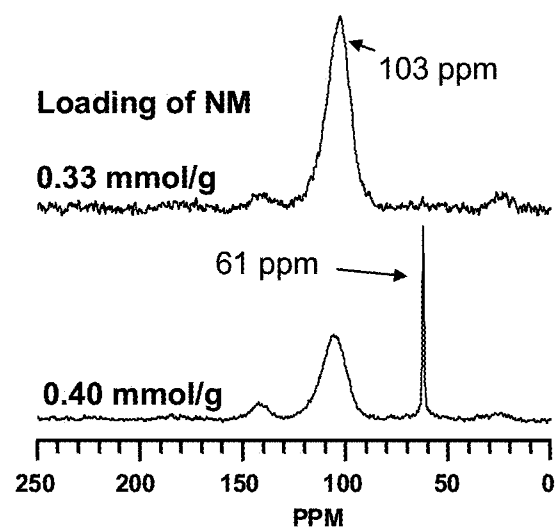
FIG. 2 shows 100 MHz $^{13}C$ NMR spectra of nitromethane-$^{13}C$ on yttrium oxide, with loadings of nitromethane-$^{13}C$ of 0.33 and 0.40 mmol/g, respectively.

$^{13}C$ solid state NMR can be used to quantify the number of aci-anion formed on metal oxides. FIG. 2 shows two $^{13}C$ NMR spectra of samples loaded with 0.33 mmol/g and 0.40 mmol/g of nitromethane-$^{13}$C. The $^{13}$C shifts for the aci-anion and physisorbed nitromethane-$^{13}$C are approximately 103 ppm and approximately 61 ppm, respectively. The amount of aci-anion present, and thus the basic site density of the MO, can be determined using the following equation, $$\text{Basic site density(mmol/g)=nitromethane-}^{13}\text{C loading}*PA_{aci\text{-}anion}/(\text{Total } PA) \quad \text{(Eq. 1)}$$

where nitromethane-$^{13}$C loading is expressed in mmol/g, $PA_{aci\text{-}anion}$ is the integrated peak area intensity(ies) for the aci-anion including each of the associated spinning side-bands, and Total PA is the integrated peak area intensity for all the peaks in the spectrum.

In FIG. 2, aside from the aforementioned $^{13}$C shifts, there is a minor peak at approximately 140 ppm. The chemical shift of this peak is consistent with (i.e., believed to represent) the formation of an anion from a dimeric nitromethane species. Nevertheless, as the dimeric nitromethane species is still believed to represent a singular interaction with one basic MO site (and as its relative intensity is relatively low in comparison to the intensity for the aci-anion), this dimeric anion peak was included in the integrated count of aci-anions. However, because the dimeric anion peak includes two carbon atoms per singular interaction, only one half of its peak area is counted. In other words, the variable $PA_{aci\text{-}anion}$ in Eq. 1 typically includes integrated peak area for the aci-anion (~103 ppm) and one-half the integrated peak area for the dimeric anion species (~140 ppm).

While the present invention has been described and illustrated by reference to particular embodiments, those of ordinary skill in the art will appreciate that the invention lends itself to variations not necessarily explicitly listed herein. As a result, reference should be made solely to the appended claims for the purpose of determining the scope of the present invention.

What is claimed is:

1. A process for converting an oxygenate-containing feed into an olefin-containing product, the process comprising:

(a) contacting a metal oxide comprising yttria with nitromethane under conditions sufficient for the nitromethane to adsorb onto the metal oxide, wherein, prior to contact with the nitromethane, the metal oxide is calcined at a temperature within the range from 250° C. to 750° C., wherein the yttria has a cubic crystal structure, and wherein the metal oxide also has a basic site density of at least 0.085 mmol/g, and a BET surface area of at least 40 m$^2$/g;

(b) analyzing the nitromethane-adsorbed metal oxide using NMR to determine a basic site density of the metal oxide;

(c) providing a catalyst system comprising a primary catalyst selected from the group consisting of aluminosilicates, aluminophosphates, silicoaluminophosphates, metal-containing derivatives thereof, and combinations thereof, and at least 30 wt % of yttria as a co-catalyst, and wherein at a given temperature of calcining the metal oxide, the catalyst lifetime increases with the loading index (“LI”);

(d) contacting the oxygenate-containing feedstock with the catalyst system under conditions sufficient to form an olefin-containing product; and (e) separating the olefin-containing product into at least ethylene and/or propylene.

2. The process of claim 1, wherein the oxygenate-containing feedstock comprises methanol and/or dimethylether.

3. The process of claim 1, wherein the basic site density of the metal oxide is at least 0.15 mmol/g.

4. The process of claim 1, wherein the primary catalyst is an aluminosilicate having a ratio of $Si/Al_2$ from 80 to 5000.

5. The process of claim 1, wherein the primary catalyst is an aluminosilicate having a ratio of $Si/Al_2$ from 100 to 4000.

6. The process of claim 1, wherein the primary catalyst is a silicoaluminophosphate having a CHA framework type, an AEI framework type, or a combination or intergrowth thereof.

7. The process of claim 1, wherein the primary catalyst is a silicoaluminophosphate having an empirical formula, on an anhydrous basis, of $Si_xAl_yP_zO_2$, wherein x is from greater than 0 to 0.25, y is from 0.4 to 0.5, and z is from 0.25 to 0.5.

8. A process for forming an olefin-containing polymer and/or oligomer, comprising:

(a) converting an oxygenate-containing feed into an olefin-containing product according to the process of claim 1; and (b) oligomerizing and/or polymerizing the ethylene and/or propylene separated from the olefin-containing product, optionally in conjunction with one or more olefin-forming catalysts, and optionally along with one or more additional comonomers, under conditions sufficient to form the olefin-containing polymer and/or oligomer.

* * * * *